(12) United States Patent
Lin et al.

(10) Patent No.: US 11,780,877 B2
(45) Date of Patent: Oct. 10, 2023

(54) METHOD OF SUGAR-GUIDED MODIFYING GLYCOSYLATED POLYPEPTIDE AND APPLICATION OF THE SAME

(71) Applicant: National Sun Yat-Sen University, Kaohsiung (TW)

(72) Inventors: Po-Chiao Lin, Kaohsiung (TW); Chih-Hung Chou, Kaohsiung (TW)

(73) Assignee: NATIONAL SUN YAT-SEN UNIVERSITY, Kaohsiung (TW)

(*) Notice: Subject to any disclaimer, the term of this patent is extended or adjusted under 35 U.S.C. 154(b) by 0 days.

(21) Appl. No.: 17/954,929

(22) Filed: Sep. 28, 2022

(65) Prior Publication Data

US 2023/0137869 A1    May 4, 2023

(30) Foreign Application Priority Data

Sep. 29, 2021   (TW) .................................. 110136324

(51) Int. Cl.
*C07K 16/00* (2006.01)
*C07K 1/107* (2006.01)

(52) U.S. Cl.
CPC ............ *C07K 1/1077* (2013.01); *C07K 16/00* (2013.01)

(58) Field of Classification Search
CPC .............................. C07K 1/1077; C07K 16/00
See application file for complete search history.

(56) References Cited

U.S. PATENT DOCUMENTS

| 6,630,577 B2 | 10/2003 | Stolowitz et al. |
| 9,678,082 B2 * | 6/2017 | Lin .................. G01N 33/54306 |
| 2016/0123988 A1 | 5/2016 | Lin et al. |

OTHER PUBLICATIONS

Chou, Chih-Hung, "Affinity directed preparation of protein macroinitiator and its application in the study of protein-polymer conjugates", Master Thesis of Department of Chemistry of National Sun Yat-sen University, Jul. 2013, Taiwan, R.O.C.

Tu, Hsiu-Chung, et al., "Direct Screening of Glycan Patterns from Human Sera: A Selective Glycoprotein Microarray Strategy", ACS Applied Bio Materials, Feb. 8, 2019, pp. 1286-1297, vol. 2.

Yang, Yung-Lin, et al., "Traceless Labeling of Glycoproteins and Its Application to the Study of Glycoprotein-Protein Interactions", ACS chemical biology, Nov. 1, 2013, pp. 390-397, vol. 9.

* cited by examiner

*Primary Examiner* — Jeanette M Lieb

(57) ABSTRACT

The present invention provides a method of sugar-guided modifying a glycosylated polypeptide. First, a boronic acid group of a probe molecule and a sugar group of the glycosylated polypeptide form a first covalent bond. Next, an alkyne group of a modifying group and an azide group of the probe molecule form a second covalent bond by adding a promoter. As a result, the modifying group can be close to the glycosylated polypeptide. Then, the modifying group can bind to a nucleophilic residue that is near the sugar group, through a nucleophilic addition reaction. The method of the present invention can selectively modify a given site with the guidance of the sugar group.

17 Claims, 7 Drawing Sheets

METHOD OF SUGAR-GUIDED MODIFYING GLYCOSYLATED POLYPEPTIDE AND APPLICATION OF THE SAME

RELATED APPLICATIONS

This application claims priority to Taiwan Application Serial Number 110136324, filed Sep. 29, 2021, which is herein incorporated by reference in its entirety.

BACKGROUND

Field of Invention

The present invention relates to a method of modifying a glycosylated polypeptide. More particularly, the present invention relates to a method of modifying a glycosylated polypeptide that is able to selectively modify a given site with the guidance of the sugar group.

Description of Related Art

Glycosylated polypeptides including general proteins, antibodies, and even peptide drugs are widely used as biomarkers or medications in contemporary medicine field. Modifying the aforementioned glycosylated polypeptides may promote their use in detection and identification, or may prolong lifetime of the glycosylated polypeptides drugs.

The conventional modification method can generally be classified into two kinds. One of them is to covalently bind to a desired modifying group for the modification by using an amine functional group of the amino acid as a nucleophilic group. However, this kind of the methods is a non-specific modification method. Since the glycosylated polypeptide has many amine functional groups on the surfaces, it is hard to control which region to be modified. Moreover, the modifying group may block the functional regions, e.g., the fragment-antigen binding (Fab) region, of the glycosylated polypeptide.

Another kind of the methods is to covalently bind to maleimide specifically by using a thiol functional group as a nucleophilic group. Although this kind of the methods is specific, it may destroy the protein structure and cause the loss of the protein bioactivities once the thiol functional group is covalently modified. This is because the thiol bond and the disulfide bond are the important functional groups for constructing the protein structure.

To improve the aforementioned disadvantages, the other conventional method is to bind one functional group including a boronic acid group to another functional group including a sulfonyl group via a linker molecule having a specific length, so as to obtain a probe molecule having boronic acid group and sulfonic ester group. The abovementioned functional group including the sulfonic ester group has a linear alkyl group with an alkyne group having at least three carbon atoms. Then, the sugar group of the target protein reacts with the boronic acid group of the probe molecule, so that the target protein binds to the probe molecule. In the meanwhile, the aforementioned linker molecule having a specific length can make the nucleophilic functional group of the target protein get close to the sulfonic ester group of the probe molecule, so that the nucleophilic functional group can perform a nucleophilic substitution reaction on the sulfonic ester group under the proximate effect. Thus, the probe molecule leaves and the target protein can be modified by the linear alkyl group with at least three carbon atoms including an alkyne group.

However, in the aforementioned method, since the reaction of the sugar group with the boronic acid group and the nucleophilic substitution reaction of the nucleophilic functional group with the sulfonic ester group occur in the same step, the sulfonic ester easily undergoes other side reactions if the concentration of the probe molecule is too high. To prevent the side reaction from occurring, the method can only be conducted at a low concentration of the probe molecule, and thus the method has an insufficient sensitivity.

Therefore, it is necessary to provide a method of sugar-guided modifying a glycosylated polypeptide, in which the binding of the probe molecule to the glycosylated polypeptide and the modification of the modifying group on the glycosylated polypeptide occur in the individual steps. Moreover, the aforementioned method can selectively modify a given site with the modifying group without changing the original structure, thereby increasing the sensitivity for subsequent applications.

SUMMARY

Accordingly, one aspect of the present invention is to provide a method of sugar-guided modifying a glycosylated polypeptide. Since the boronic acid group of the probe molecule and the sugar group of the glycosylated polypeptide forms affinity covalent binding, and the reaction of the probe molecule with the modifying group is controlled by using a specific promoter, the binding of the glycosylated polypeptide with the probe molecule and the modification of the glycosylated polypeptide by the modifying group are performed in the individual steps. Therefore, the region adjacent to a sugar group is modified by the modifying group.

Another aspect of the present invention is to provide a reagent kit of sugar-guided antibody modification, which modifies the antibody constant (fragment crystallizable, Fc) region of the antibody specifically by the modifying group with the abovementioned method of sugar-guided modifying a glycosylated polypeptide, in which the antibody is used as an example for the glycosylated polypeptide.

According to the aforementioned aspect, a method of sugar-guided modifying a glycosylated polypeptide is provided. In one embodiment, a glycosylated polypeptide including at least one amino acid having a nucleophilic residue is provided at first. Next, a boronic acid group of a probe molecule reacts with a sugar group of the glycosylated polypeptide to form a first intermediate product having a first covalent bond. The molar concentration ratio of the glycosylated polypeptide and the probe molecule is 1:1000 to 1:1, and the aforementioned probe molecule includes a structure as shown in a formula (I):

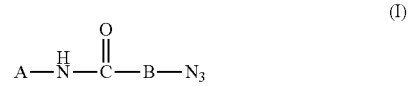

in the formula (I), A has structures as shown in formulas (I-1-1) to (I-1-3), B has a structure as shown in a formula (I-2), and sulfonyl group of B binds to an azide group of the probe molecule,

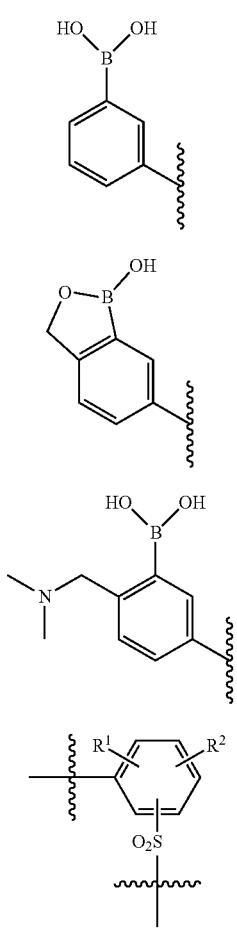

in the formula (I-2), R¹ is a hydrogen atom, a halogen atom or an alkyl group having 1 to 3 carbon atoms, R² is a hydrogen atom or a halogen atom.

Then, the azide group of the probe molecule reacts with an alkyne group of a modifying group in the presence of a promoter, so as to form a second intermediate product having a second covalent bond, in which the aforementioned promoter includes a catalyst.

The aforementioned catalyst is a metallic salt of monovalent copper or divalent copper.

The aforementioned glycosylated polypeptide of the second intermediate product connects to the probe molecule via the first covalent bond and connects to the modifying group via the second covalent bond, respectively.

Then, a polyol compound is added to form a third intermediate product. The aforementioned the polyol compound is at least one selected from the group consisting of glycerol, sorbitol and polyethylene glycol (PEG), and in the third intermediate product, the glycosylated polypeptide connects to the probe molecule and the modifying group via the second covalent bond.

Furthermore, a hydrolysis reaction is performed on the third intermediate product to release the probe molecule, thereby forming the glycosylated polypeptide having a modifying group.

According to one embodiment of the present invention, the aforementioned modifying method further includes dissolving the glycosylated polypeptide and the probe molecule in the salt buffer; removing an unreacted probe molecule after forming the aforementioned first intermediate product having the first covalent bond; and removing an unreacted modifying group after the hydrolysis reaction.

According to one embodiment of the present invention, the aforementioned catalyst can be selected from the group consisting of tetrakis(acetonitrile)copper(I) hexafluorophosphate [Cu(CH₃CN)₄PF₆], copper(I) iodide (CuI) and copper (II) sulfate (CuSO₄).

According to one embodiment of the present invention, the promoter further includes tris[(1-benzyl-1H-1,2,3-triazol-4-yl) methyl]amine (TBTA), reductant or a combination thereof when the catalyst is tetrakis(acetonitrile)copper (I) hexafluorophosphate, and the reductant is tris(2-carboxyethyl)phosphine (TCEP) or sodium ascorbate (NaAsc).

According to one embodiment of the present invention, the aforementioned promoter further includes a reductant when the catalyst is copper(II) sulfate, and the reductant can be tris(2-carboxyethyl)phosphine (TCEP) or sodium ascorbate (NaAsc).

According to one embodiment of the present invention, the aforementioned modifying group can include a labeling reagent, a polymer with a number average molecular weight of 600 Da to 40 kDa, a polypeptide or an alkyl halide.

According to another aspect, an reagent kit of sugar-guided antibody modification is provided, in which the kit includes a target antibody, a probe molecule, a promoter, a modifying group, a polyol compound and a hydrolysis agent. The antibody constant region (Fc region) of the aforementioned target antibody includes a sugar group and at least one amino acid having a nucleophilic residue.

The molar concentration ratio of the aforementioned target antibody and the probe molecule is 1:1000 to 1:1, and the probe molecule has a structure as shown in the following formula (I):

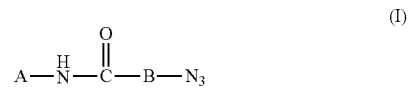

in the formula (I), A can have structures as shown in the formulas (I-1-1) to (I-1-3), B can have a structure as shown in a formula (I-2), and sulfonyl group of B binds to azide group of the probe molecule,

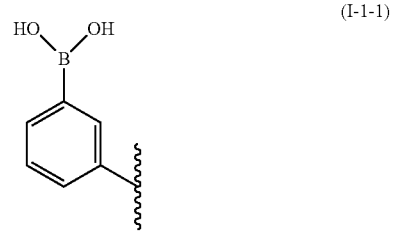

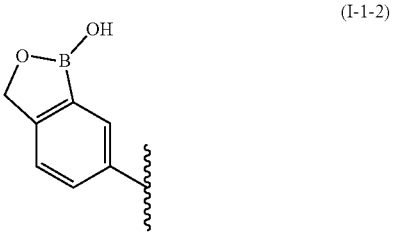

-continued

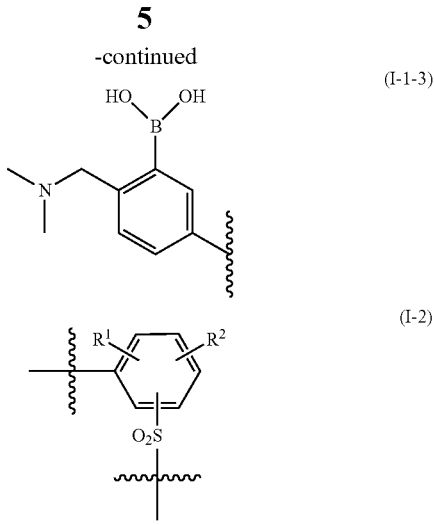

(I-1-3)

(I-2)

in the formula (I-2), $R^1$ is a hydrogen atom, a halogen atom or an alkyl group having 1 to 3 carbon atoms, $R^2$ can be a hydrogen atom or a halogen atom, in which a boronic acid group of the probe molecule and the sugar group of the target antibody, so as to form a first intermediate product having a first covalent bond.

The aforementioned promoter can include a catalyst, and the catalyst can be selected from the group consisting of tetrakis(acetonitrile)copper(I) hexafluorophosphate [Cu(CH$_3$CN)$_4$PF$_6$], copper(I) iodide (CuI) and copper(II) sulfate (CuSO$_4$).

The aforementioned modifying group can have an alkyne group, and the aforementioned alkyne group and the azide group of the probe molecule can form a second intermediate product having a second covalent bond in the presence of the catalyst. In the second intermediate product, the target antibody connects to the probe molecule via the first covalent bond and connects to the modifying group via the second covalent bond, respectively.

The aforementioned polyol compound can be used to form a third intermediate product, in which the polyol compound can be at least one selected from the group consisting of glycerol, sorbitol and polyethylene glycol, and the target antibody is connected to the probe molecule and the modifying group via the second covalent bond in the third intermediate product.

The aforementioned hydrolysis agent can be used to perform a hydrolysis reaction on the third intermediate product to release the probe molecule, thereby forming the target antibody with an antibody constant region modified by the modifying group. The aforementioned hydrolysis agent is an acidic hydrolysis agent.

According to one embodiment of the present invention, the promoter further includes tris[(1-benzyl-1H-1,2,3-triazol-4-yl) methyl]amine (TBTA), a reductant or a combination thereof when the catalyst is the tetrakis(acetonitrile)copper(I) hexafluorophosphate, and the aforementioned reductant can be tris(2-carboxyethyl)phosphine (TCEP) or sodium ascorbate (NaAsc).

According to one embodiment of the present invention, the promoter can further include the aforementioned reductant when the catalyst is copper(II) sulfate, and the aforementioned reductant can be tris(2-carboxyethyl)phosphine (TCEP) or the sodium ascorbate (NaAsc).

According to one embodiment of the present invention, the modifying group includes a labeling reagent, a polymer with a number average molecular weight of 600 Da to 40 kDa, polypeptide or an alkyl halide.

According to one embodiment of the present invention, the reagent kit of sugar-guided antibody modification further includes a salt buffer.

In practice with the method of sugar-guided modifying glycosylated polypeptide and application of the same, the sugar group on the glycosylated polypeptide is used for guiding, and the specific promoter is used to control the reaction of the probe molecule with the modifying group. As a result, the binding of the glycosylated polypeptide to the probe molecule and the modification of the glycosylated polypeptide by the modifying group can occur in the individual steps. Therefore, the nucleophilic residue adjacent to the sugar group can be modified with the modifying group. Thus, method of the present invention can selectively modify a given site with the guidance of the sugar group, thereby exposing the functional regions of the glycosylated polypeptide.

BRIEF DESCRIPTION OF THE DRAWINGS

The invention can be more fully understood by reading the following detailed description of the embodiment, with reference made to the accompanying drawings as follows.

DETAILED DESCRIPTION

The invention provides a method of sugar-guided modifying a glycosylated polypeptide and application of the same. Within the aforementioned method, the sugar group on the glycosylated polypeptide is used for guiding, and the specific promoter is used to control the reaction of the probe molecule with the modifying group. As a result, the binding of the glycosylated polypeptide to the probe molecule and the modification of the glycosylated polypeptide by the modifying group can occur in the individual steps. Therefore, the nucleophilic residue adjacent to the sugar group can be modified by the modifying group. Thus, the modifying group can specifically modify the glycosylated polypeptide, thereby preventing the modifying group from blocking the functional region (i.e., a modified region for selectively binding the modifying group) of the glycosylated polypeptide. As a result, the application for the glycosylated polypeptide having the modifying group can be more flexible. Besides, the operation of releasing the probe molecule will not affect the structure of the sugar group on the glycosylated polypeptide.

In the method of the present invention, the sugar group of the glycosylated polypeptide and the boronic acid group of the probe molecule are used to form a first intermediate product having a first covalent bond. Next, the modifying group and the probe molecule form a second intermediate product having a second covalent bond by adding a promoter. Then, in the second intermediate product, an amino acid having a nucleophilic residue adjacent to the sugar group performs a nucleophilic addition reaction with the nucleophilic residue, so as to form a third intermediate product having a third covalent bond.

After that, the boronic acid group of the probe molecule can be released from the sugar group of the glycosylated polypeptide by adding the polyol compound, thereby forming a third intermediate product. Then, a hydrolysis agent is added to perform a hydrolysis reaction on the third intermediate product, so that the probe molecule is released from the glycosylated polypeptide. As a result, the nucleophilic residue of the glycosylated polypeptide adjacent to a sugar group is modified by the modifying group.

The term "guide" referred in the present invention means to use probe molecule as a media to guide the modifying group to a region nearby the sugar group, so that the modifying group is ensured to be modified at the amino acid having a nucleophilic residue adjacent to the sugar group.

The term "specifically modify" referred in the present invention means that the nucleophilic residue adjacent to the aforementioned sugar group can be modified by the modifying group according to the location of the sugar group on the glycosylated polypeptide. Since the region to be modified by the modifying group can be determined in accordance to the sugar group, to "specifically modify" is said to be a modification with specificity or to have a modifying specificity herein.

The "functional region" referred in the present invention means the region where the glycosylated polypeptide and its substrate bind or the fragment-antigen binding (Fab) region where the antibody and the antigen bind, etc., for example.

The "to perform in individual steps" referred in the present invention means that the two reactions are not performed in the same time. Instead, a specific reagent is required after the prior reaction is completed to perform another reaction. The "specific reagent" referred herein will be elaborate hereafter.

It is noted that the concentrations or the values of the concentrations of various reagent (not including solution or buffer) mentioned herein refer to the final concentrations of the mixed solutions.

The aforementioned glycosylated polypeptide can include but be not limited to a synthetic or a natural protein, a linear or a cyclic polypeptide, a linear or a cyclic peptide drug, etc., having sugar groups exposing to their surfaces. Among them, the aforementioned protein includes an antibody, and the aforementioned antibody can be a monomer, a dimer, a trimer, a tetramer, a pentamer or a hexamer. Thus, the molecular weight of the aforementioned protein or polypeptide can be 30 kDa to 1000 kDa. Preferably, the molecular weight can be 30 kDa to 150 kDa.

In one embodiment, the concentration of the aforementioned glycosylated polypeptide can be 0.1 μM to 1 mM, for example.

The sugar group of the aforementioned glycosylated polypeptide can be a monosaccharide, a linear or branched oligosaccharide or polysaccharide, and the sugar group can be an N-bond sugar group or an O-bond sugar group. Besides, since the sugar group is used to form an affinity covalent binding with the boronic acid group of the probe molecule in the present invention, the sugar group referred herein should be exposed to the surface of the glycosylated polypeptide for the formation of the bond.

The aforementioned amino acid having a nucleophilic residue can include a tyrosine (Tyr), an aspartic acid (Asp), a histidine (His), a glutamine (Glu), a lysine (Lys), an arginine (Arg), a serine (Ser) and a cysteine (Cys).

The aforementioned probe molecule has a structure as shown in a formula (I):

(I)

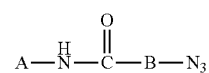

(I-1-1)

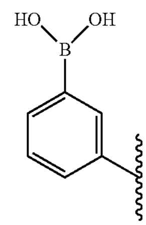

(I-1-2)

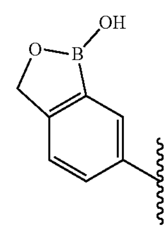

(I-1-3)

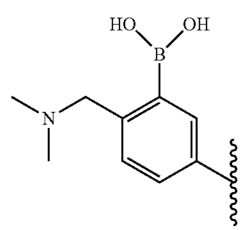

(I-2)

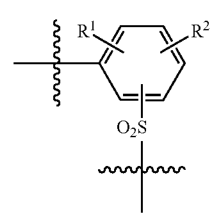

in the formula (I), A has structures as shown in formulas (I-1-1) to (I-1-3), B has a structure as shown in a formula (I-2), and the sulfonyl group binds to the azide group, in the formula (I-2), $R^1$ can be a hydrogen atom, a halogen atom or an alkyl group having 1 to 3 carbon atoms, and $R^2$ is a hydrogen atom or a halogen atom.

In one embodiment, the concentration of the aforementioned probe molecule can be 1 μM to 1 mM. If the concentration of the probe molecule is lower than 1 μM, the efficiency of the subsequent modification with the modifying group will not be good, resulting in the disadvantage of the poor effect (e.g., fluorescent labeling or prolonging the lifetime of the glycosylated polypeptide) of the modifying group.

The aforementioned modifying group has an alkyne group which performs a cycloaddition reaction with an azide group of the aforementioned probe molecule, so as to form a second covalent bond. The modifying group can include a labeling reagent, a polymer with a number average molecular weight of 600 Da to 40 kDa, a polypeptide or an alkyl halide.

In one embodiment, the concentration of the modifying group can be 1 μM to 1 mM.

It is noted that the selection of the modifying group is determined by the aim and the experimental design. Thus, various modifying groups used for the method of the present invention should fall within the scope of the claim of the present invention. For example, a modifying group with fluorescence can be selected to make more easily to observe the glycosylated polypeptide. Moreover, the conventional polymer that prolongs the lifetime of the glycosylated polypeptide can be selected to achieve the aforementioned aim. More details for the polymer will be elaborate in the followings.

Figure 1A:
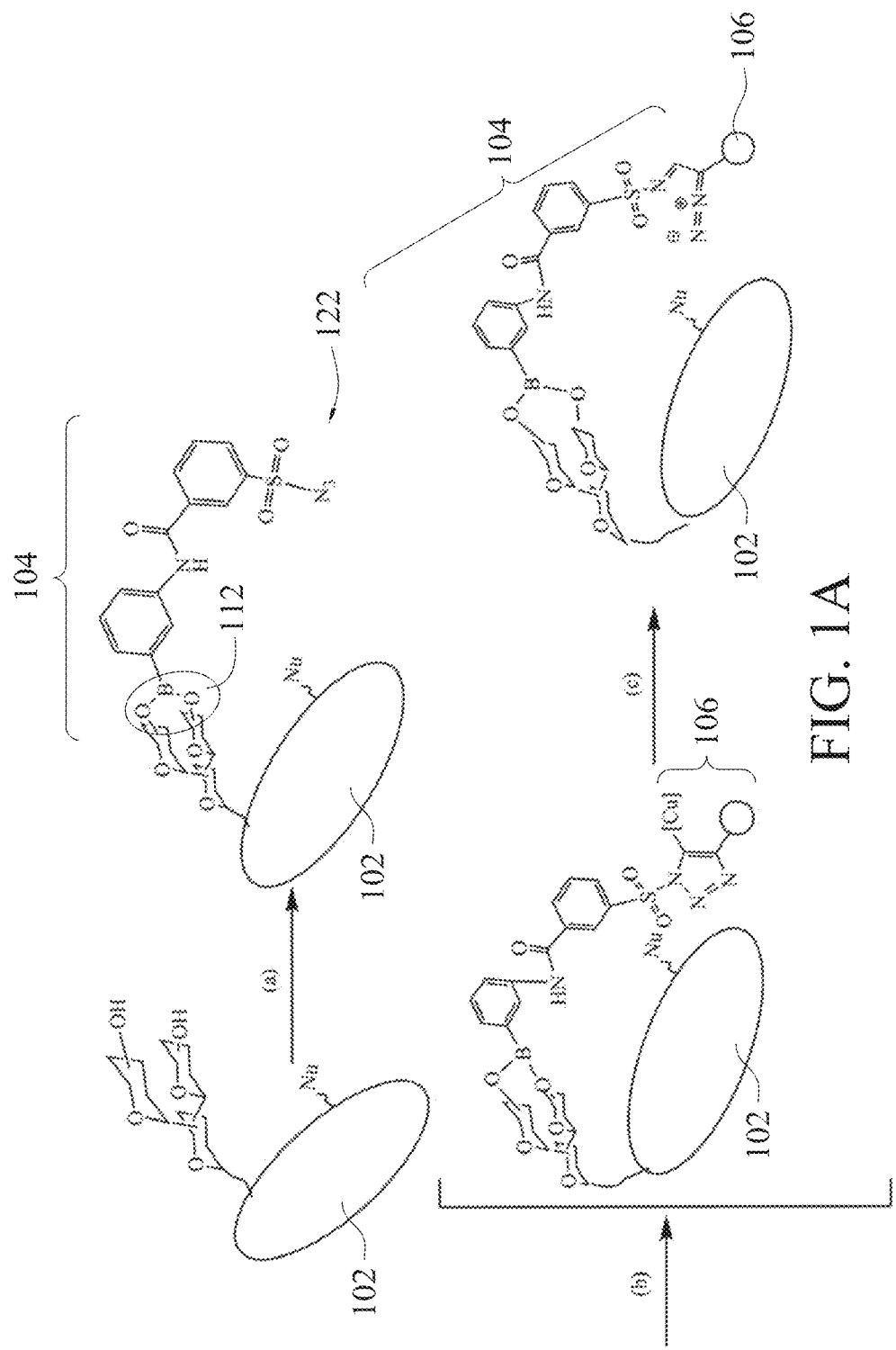
FIGS. 1A to 1B are flowcharts illustrating the method of sugar-guided modifying a glycosylated polypeptide in accordance with an embodiment of the present invention.
Figure 1B:
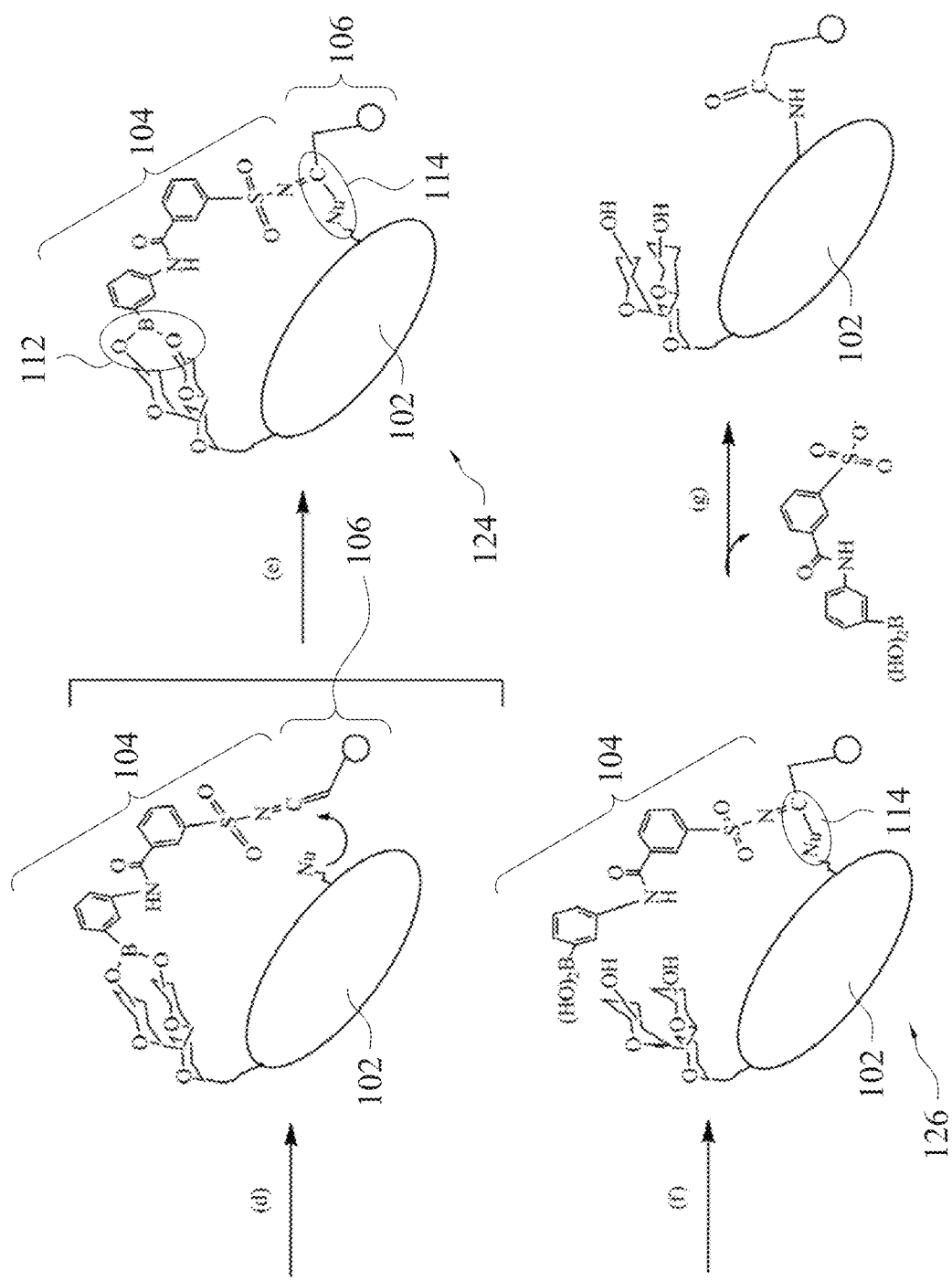

It is noted that the methylamide group is used as a linker molecular for the alkyne group of the aforementioned modifying group (as shown in FIG. 1B). However, for those skilled in the art, any conventional chemical method can be used to connect the modifying group to the alkyne group, and the aforementioned linker molecule can be a linear molecular at any length depending merely on the experimental requirement.

The aforementioned labeling reagent can be any conventional reagent or commercial products, e.g., a green fluorescent protein (GFP) or a biotin having a fluorescent molecular or labelled by an isotope, etc.

The aforementioned polymer can be polyesters, polyols, polyamides, polysaccharides, polyamino acids and the like. In one example, the polymer preferably can be polymers with biocompatibility whose average molecular weight is 1 kDa to 40 kDa. The specific examples of the aforementioned polymer with biocompatibility can include but be not limited to polyethylene glycol (PEG), polylactic acid (PLA), polyglycolide (PGA), polycaprolactone (PCL), polymethacrylamide, polyvinyl alcohol, polycarboxylate, polyvinylpyrrolidone, dextran, cellulose, chitosan, hydroxyethyl starch (HES) or polyglutamic acid, etc.

The aforementioned polypeptide is consisted of at least 100 to 3000 amino acids. Besides, the specific examples of the aforementioned polypeptide can include but be not limited to human glucagon-like peptide-1 (GLP-1), exenatide, human glucagon-like-peptide-2 (GLP-2), C-peptide, calcitonin, human parathyroid hormone (PTH), glucagon, granulocyte colony stimulating factor (G-CSF), granulocyte-macrophage colony stimulating factor (GM-CSF), interferon, interleukin, vascular endothelial growth factor (VEGF) receptor, tumor necrosis factor-alpha (TNF-α) receptor, growth hormone, erythropoietin and coagulation factors.

The aforementioned alkyl halide is used as a macroinitiator, and the specific examples can include but be not limited to 2-azidoethyl 2-bromoisobutyrate, bis[2-(2'-bromoisobutoxy)ethyl]disulfide, bis[2-(2'-bromoisobutoxy)undecyl] disulfide, 2-bromoisobutyric anhydride, α-bromoisobutyl bromide, ethyl 2-(2-bromoisobutoxy) methylpropionate, tert-butyl-α-bromoisobutyrate, 3-butynyl-2-bromoisobutyrate, dodecyl-2-bromoisobutyrate, ethyl-α-bromoisobutyrate, vinyl-bis(2-bromoisobutyrate), 2-hydroxyethyl-2-bromoisobutyrate, methyl α-bromoisobutyrate, octadecyl-2-bromoisobutyrate, etc.

After the glycosylated polypeptide is modified by the aforementioned macroinitiator, the aforementioned polymer can be polymerized on the glycosylated polypeptide in the manner of atom transfer radical polymerization (ATRP). The operating method of ATRP is well known to those skilled in the art and will not be elaborated herein.

When the aforementioned modifying group is a labeling reagent, the labeling efficiency of the modifying group on the glycosylated polypeptide can be effectively promoted without destroying the structure of the glycosylated polypeptide, thereby dramatically increasing the sensitivity for label detection. When the aforementioned modifying group is a polymer, a polypeptide or an alkyl halide, the glycosylated polypeptide can be modified by the conventional molecular that is able to delay the degradation of glycosylated polypeptide with the method of the present invention, thereby prolonging the lifetime of the glycosylated polypeptide without destroying the structure or effecting the activity of the glycosylated polypeptide.

The aforementioned promoter includes a catalyst, tris[(1-benzyl-1H-1,2,3-triazol-4-yl)methyl]amine (TBTA) and a reductant.

The aforementioned catalyst can be a metallic salt of monovalent copper or divalent copper. Preferably, the aforementioned catalyst is selected from the group consisting of tetrakis(acetonitrile)copper(I) hexafluorophosphate [Cu(CH$_3$CN)4PF6](Cu(CH$_3$CN)$_4$PF$_6$), copper(I) iodide(CuI) and copper(II) sulfate(CuSO$_4$). In one embodiment, the concentration of the catalyst can be 0.1 mM to 1 mM.

The concentration of the aforementioned tris[(1-benzyl-1H-1,2,3-triazol-4-yl) methyl]amine (TBTA) can be 0.1 mM to 1 mM, and the TBTA is used as a catalyst stabilizer. The oxidation of the catalyst can be prevented by adding tris[(1-benzyl-1H-1,2,3-triazol-4-yl) methyl]amine (TBTA).

The aforementioned reductant can be tris(2-carboxyethyl) phosphine (TCEP) or sodium ascorbate (NaAsc). In one embodiment, the concentration of the reductant can be 0.1 mM to 1 mM.

The promoter further includes tris[(1-benzyl-1H-1,2,3-triazol-4-yl) methyl]amine (TBTA), a reductant or the combination thereof when the aforementioned catalyst is tetrakis (acetonitrile)copper(I) hexafluorophosphate [Cu(CH3CN) 4PF6].

When the aforementioned catalyst is copper(II) sulfate, the promoter includes the aforementioned reductant.

If the aforementioned promoter is not added, the modifying group cannot react with the probe molecule, and the glycosylated polypeptide cannot be modified by the modifying group.

The aforementioned polyol compound is at least one selected from the group consisting of glycerol, sorbitol and polyethylene glycol (PEG).

The aforementioned hydrolysis agent can be an acid hydrolysis agent. The specific examples of the aforementioned hydrolysis agent can include but be not limited to a solution with 1 M HCl dissolved in 1,4-dioxane, a tris buffer (pH 10) or a potassium carbonate solution.

Referring to FIGS. 1A to 1B. FIGS. 1A to 1B are flowcharts illustrating the method of sugar-guided modifying glycosylated polypeptide in accordance with an embodiment of the present invention. First, as shown in step (a) of FIG. 1A, the glycosylated polypeptide 102 reacts with the probe molecule 104, so as to form a first intermediate product 122 having a first covalent bond 112. The details about the glycosylated polypeptide 102 and the probe molecule 104 are elaborated in the prior paragraph and will not be elaborated again herein.

The aforementioned first covalent bond 112 is formed by performing the nucleophilic addition reaction with the cis-dihydroxy group of the sugar group of the glycosylated polypeptide 102 and the boronic acid group on the probe molecule 104, and the first covalent bond 112 is a boronate diester bond.

Then, as shown in step (b) of FIG. 1A and step (d) of FIG. 1B, the modifying group 106 and the aforementioned promoter are added, so that the second covalent bond 114 of the second intermediate product 124 is formed by the cycloaddition reaction of the alkyne group on the modifying group 106 with the azide group of the probe molecule 104. Step (c) and step (d) illustrate the transition state in the process of forming the second intermediate product 124 having the second covalent bond 114, and are elaborated separately in the following.

As shown in FIG. 1A, the aforementioned alkyne group forms a triazole group with the azide group after the modifying group 106 and the promoter are added in step (b). Then, in the step (c), the ring of the triazole group opens after the triazole group is subjected to a resonance and an electron transfer. Then, a ketenimine forms in the step (d) of FIG. 1B after the molecular nitrogen ($N_2$) and the copper of the promoter are removed from the triazole with an open ring.

The specific examples and the working conditions related to the modifying group 106 and the promoter are elaborated above and will not be repeated again.

Next, as shown in step (e) of FIG. 1B, the nucleophilic residue (Nu) on the glycosylated polypeptide 102 performs a nucleophilic addition reaction on the ketenimine, so as to form a second intermediate product 124 having a second covalent bond 114. At this time, in the second intermediate product 124, the glycosylated polypeptide 102 binds to the probe molecule 104 via the first covalent bond 112 and binds to the modifying group 106 via the second covalent bond 114.

Then, as shown in step (f) of FIG. 1B, the polyol compound is added into the second intermediate product 124 to form the third intermediate product 126. After the step (f), the glycosylated polypeptide 102 binds to the probe molecule 104 and the modifying group 106 merely via the second covalent bond 114. In other words, the boronic acid group of the probe molecule 104 is released from the sugar group of the glycosylated polypeptide 102 after the polyol compound is added.

With the aforementioned polyol compound, the boronic acid group of the probe molecule can be released from the sugar group of the glycosylated polypeptide without destroying its original structure.

Then, as shown in step (g) of FIG. 1B, the hydrolysis agent is added into the third intermediate product 126, so that the carbon-nitrogen double bond of the third intermediate product 126 is hydrolyzed to form the carbonyl group, thereby releasing the probe molecule 104 from the glycosylated polypeptide 102.

It is noted that the aforementioned reaction can be performed in a 0.1 M, pH 8 salt buffer including 10% (v/v) dimethyl sulfoxide (DMSO), in which the specific examples of the salt buffer can include but be not limited to a phosphate buffered saline (PBS), a tris(hydroxymethyl)aminomethane-buffered saline (TBS) or a glycine buffered saline, etc., and the working condition of the salt buffer is well known to those skilled in the art and can be adjusted easily. A simplified illustration is provided herein without intending to limit the scope of the present invention.

The method of the present invention is to modify an amino acid having a nucleophilic residue adjacent to a sugar group by a modifying group guided by the sugar group. Thus, the method of the present invention can selectively modify a given site.

Besides, in the present invention, the binding of the probe molecule to the glycosylated polypeptide and the binding of the modifying group to the probe molecule occur in the individual steps, so that the modifying group can be guided and be allowed to bind to the glycosylated polypeptide. As a result, the sulfonyl group on the probe molecule would not undergo other undesired reactions due to the probe molecule at an excessive high concentration. Thus, the probe molecule in the present invention can have a wider range of the concentration, thereby overcoming the problem of insufficient sensitivity of the conventional methods whose concentration of probe molecule is not allowed to increase.

The other aspect of the present invention provides a reagent kit of sugar-guided antibody modification. The aforementioned reagent kit includes a target antibody, a probe molecule, a promoter, a modifying group, a polyol compound and a hydrolysis agent. In one embodiment, the aforementioned reagent kit can further include a salt buffer. The information of the specific working method, the use amount and the kinds regarding the probe molecule, the promoter, the modifying group, the polyol compound, the hydrolysis agent and the salt buffer, etc., is elaborated above and will not be repeated again. The target antibody referred herein the present invention belongs to one kind of the aforementioned glycosylated polypeptides, and the information such as the specific use method, the use amount and the kind thereof can be referred to what has stated above. In this aspect, since the sugar group of the antibody is mainly distributed in the antibody constant region (Fc region), it is the antibody constant region, but not the fragment antigen binding (Fab) region, that can be modified by the modifying group specifically. Thus, the reagent kit can effectively prevent the modifying group with a high molecular weight from blocking the Fab region, thereby modifying the antibody without affecting the binding force of the antibody to the antigen.

Several examples are provided to describe method of sugar-guided modifying a glycosylated polypeptide of the present invention and application of the same. However, it will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the followed claims.

Synthesis of a Probe Molecule

Synthesis Example A-1

Figure 2:
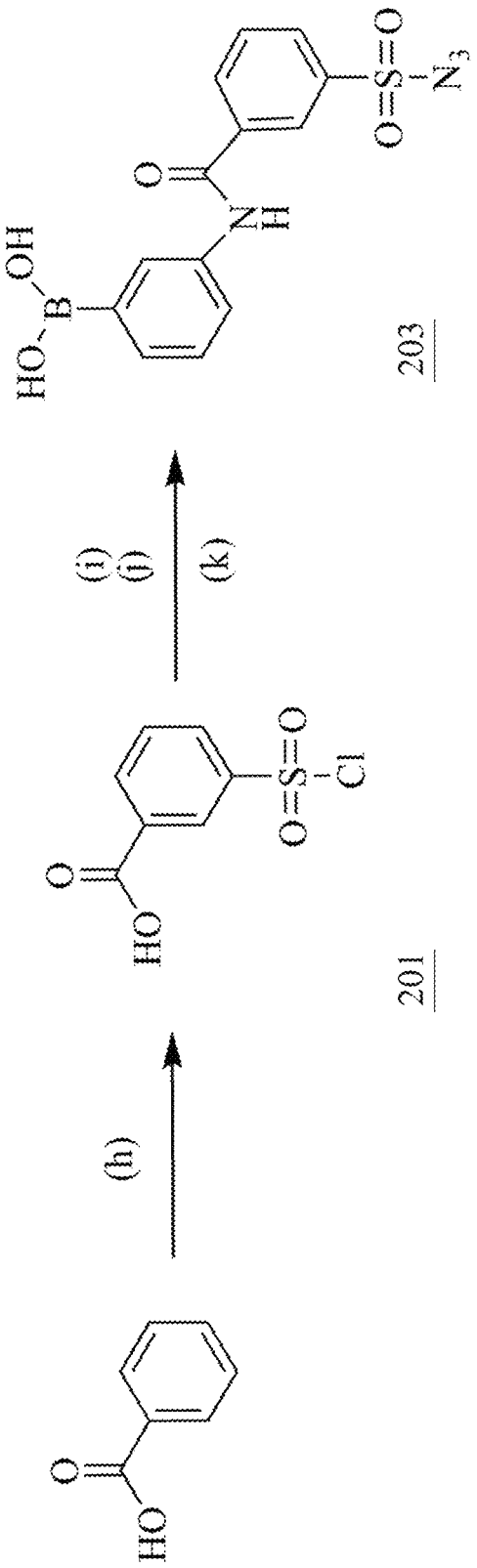
FIG. 2 is a flowchart illustrating the method of synthesizing a probe molecule in accordance with a synthesis example of the present invention.

Referring to FIG. 2, which was a flowchart illustrating the synthesis of a probe molecule 203 in accordance with an embodiment of the present invention. First, as shown in FIG. 2, the benzoic acid was added to chlorosulfuric acid, followed by a heat refluxing reaction to form a compound 201. Then, in step (i), thionyl chloride was added to a round-bottom flask to perform the heat refluxing reaction, and the solvent was abstracted after the reaction completed, followed by the addition of dehydrated molecular sieve and tetrahydrofuran. Then, in step (j), N,N-diisopropylethylamine, 3-aminophenyl boronic acid and tetrahydrofuran were added in another round-bottom flask and mixed evenly to obtain a mixed solution, which was then added slowly to the round-bottom flask containing the compound 201, molecular sieve and tetrahydrofuran, so as to perform a coupling reaction for 30 minutes. After the coupling reaction was completed, the molecular sieve was removed and the solvent was dried by suction filtration to obtain a dried compound. After that, in step (k), ketone was added to dissolve the aforementioned dried compound, and the sodium azide dissolved in water was added slowly with a separatory funnel. After an overnight reaction, the solvent was removed, followed by a separation with a chromatographic column to form a probe molecule 203 of a synthesis example A-1.

Synthesis of a Modifying Group

Synthesis Example

Figure 3:
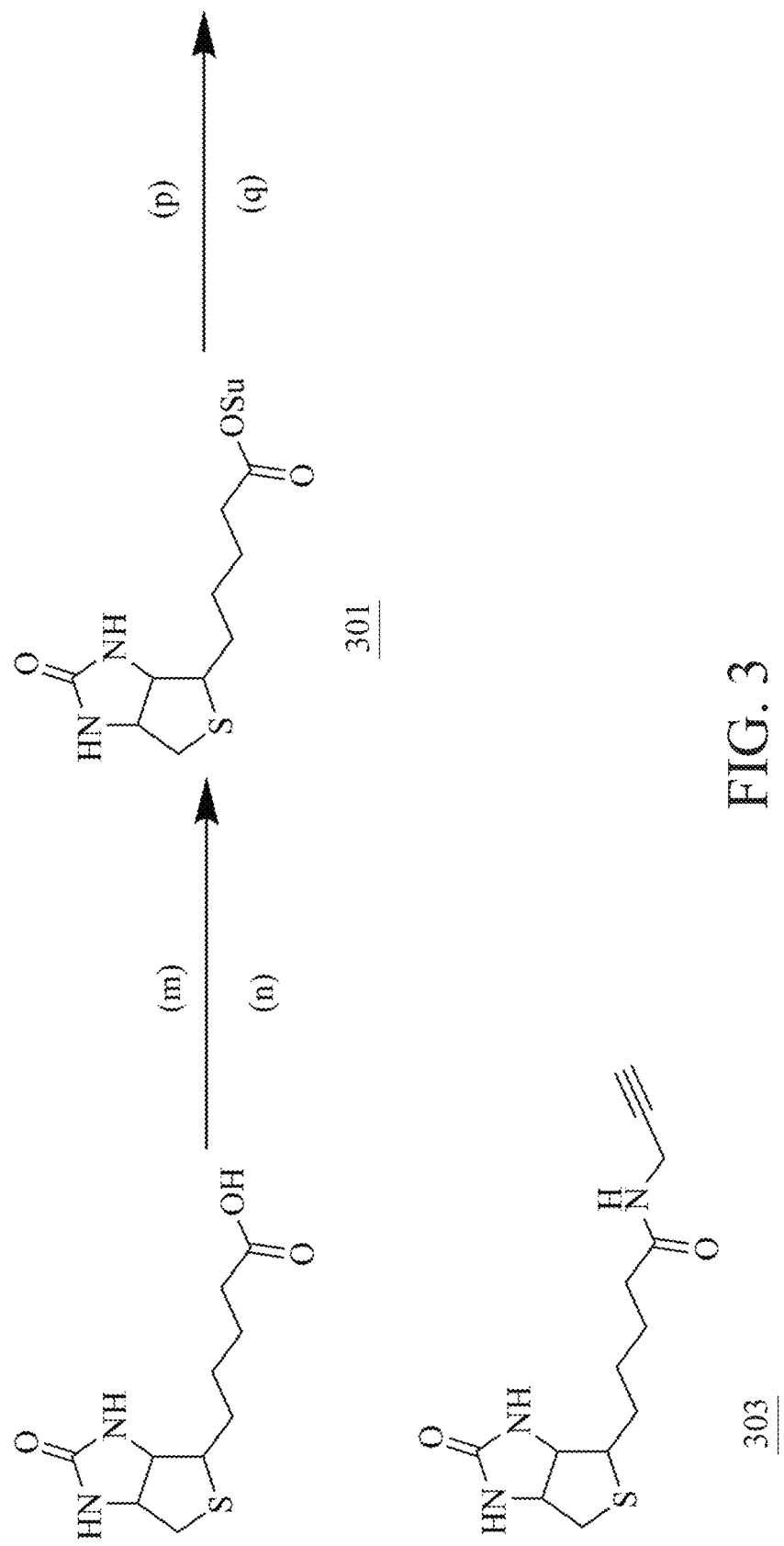
FIG. 3 is a flowchart illustrating a method of synthesizing a modifying group in accordance with a synthesis example of the present invention.

Referring to FIG. 3, which was a flowchart illustrating the synthesis of a modifying group 303 in accordance with an embodiment of the present invention. As shown in FIG. 3, a biotin (product name: FB02633; made by Carbosynth Ltd.) was dissolved in N,N-dimethylformamide at first, followed by the addition of 1-ethyl-3-(3-dimethylaminopropyl)carbodiimide and N-hydroxysuccinimide sequentially, so that the final concentration of the biotin is 500 µM. After an overnight reaction, in step (n), the solvent was abstracted and removed, followed by a five-times of extraction using water and methylene chloride at a ratio of 1:5 to collect the organic layer, which was then dehydrated by magnesium sulfate and subjected to a suction filtration, so as to remove the solvent, thereby forming a compound 301. Next, in step (p), the aforementioned compound 301 was dissolved in N,N-dimethylformamide and reacted with propargylamine and N,N-diisopropylethylamine at room temperature for 24 hours. After that, in step (q), the solvent was abstracted and removed, followed by three times of extractions using water and methylene chloride at a ratio of 1:3, so as to collect the organic layer, which was then dehydrated by magnesium sulfate. Then, a chromatographic column was used for separation to obtain a modifying group 303 of a synthesis example B-1.

Evaluating Efficiency of Modification of Glycosylated Polypeptide with Modifying Group

Example 1

The fetuin and the probe molecule of the synthesis example A-1 was dissolved in a 0.1 M, pH 8 phosphate buffered saline (PBS) including 10% dimethyl sulfoxide (DMSO) to form a first mixed solution, followed by a reaction at room temperature for 24 hours, in which the concentration of the fetuin in the first mixed solution was 50 µM, and the concentration of the probe molecule of the synthesis example A-1 was 500 µM. Then, a centrifugal filter device (Amicon Ultra-0.5 ml 10 K) was used to separate unreacted probe molecule with a centrifugal speed at 15000 rpm.

Next, the modifying group of the synthesis example B-1, tetrakis(acetonitrile)copper(I) hexafluorophosphate [Cu (CH3CN)4PF6] and tris[(1-benzyl-1H-1,2,3-triazol-4-yl) methyl]amine (TBTA) were added to form a second mixed solution, followed by a reaction under room temperature for 48 hours, in which the concentration of the modifying group of the synthesis example B-1 in the second mixed solution was 500 µM, the concentration of tetrakis(acetonitrile)copper(I) hexafluorophosphate [Cu(CH$_3$CN)4PF6] was 1 mM, and the concentration of tris[(1-benzyl-1H-1,2,3-triazol-4-yl) methyl]amine (TBTA) was 1 mM. Next, 10% glycerol and pH 8.0 to 10.0 PBS buffer were added. Then, after the unreacted modifying group of the synthesis example B-1 was removed by a centrifugation at 15000 rpm with a centrifugal filter device, the glycosylated polypeptide included a modifying group. Each of the ingredients and the condition used in Example 1 were elaborated in Table 1.

Examples 2 to 8 and Comparative Examples 1 to 5

Examples 2 to 8 and comparative examples 1 to 5 were obtained using the same method to obtain the example 1 besides the use amounts and kinds of each used ingredients were different. The ingredients and their use amounts used in examples 2 to 8 and comparative examples 1 to 5 were shown in Table 1 and would not be repeated again herein.

The results of evaluation of examples 1 to 8 and the comparative examples 1 to 5 were shown in FIGS. 4A to 6B.

Evaluation Method

1. Efficiency of Modification with Modifying Group

To obtain gels, the glycosylated polypeptides having the modifying groups of examples 1 to 8 and the comparative examples 1 to 4 in present invention were subjected to a sodium dodecyl sulfate polyacrylamide gel electrophoresis (SDS-PAGE). The obtained gels were subjected to coomassie brilliant blue and Western blotting respectively, in which Western blotting was performed with the antibody (Product name: A0185; made by Sigma-Aldrich) of the modifying group (biotin) of the synthesis example B-1. Then, the results of the aforementioned two methods were compared to each other with the evaluation method shown in the following:

The bands formed in both coomassie brilliant blue stain and Western blotting means that the glycosylated polypeptide was exactly modified by modifying group, and in the Western blotting, the darker the color was, the better the efficiency of the modification was.

The band formed in coomassie brilliant blue stain but not Western blotting means that the glycosylated polypeptide was not modified by the modifying group.

Figure 4A:
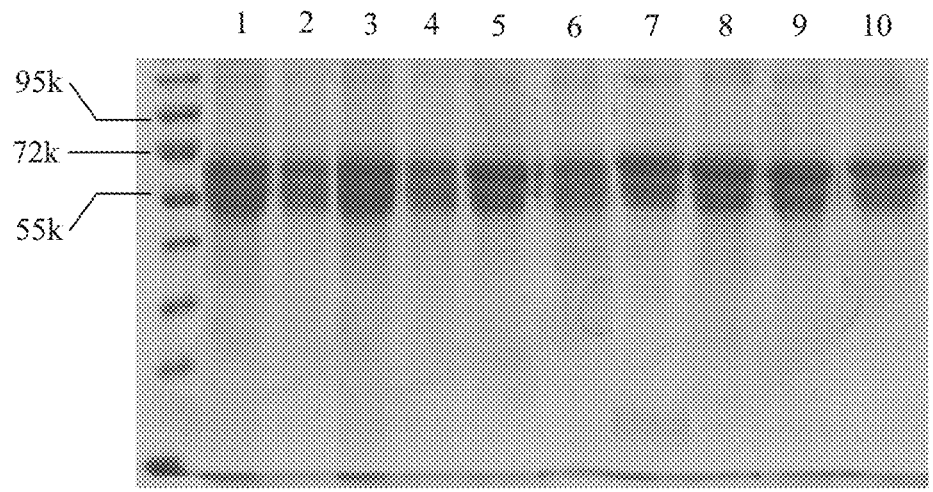
FIG. 4A is a sodium dodecyl sulfate polyacrylamide gel electrophoresis (SDS-PAGE) stained by coomassie blue showing the efficiency of the modification of the glycosylated polypeptide in accordance with an embodiment of the present invention.
Figure 4B:
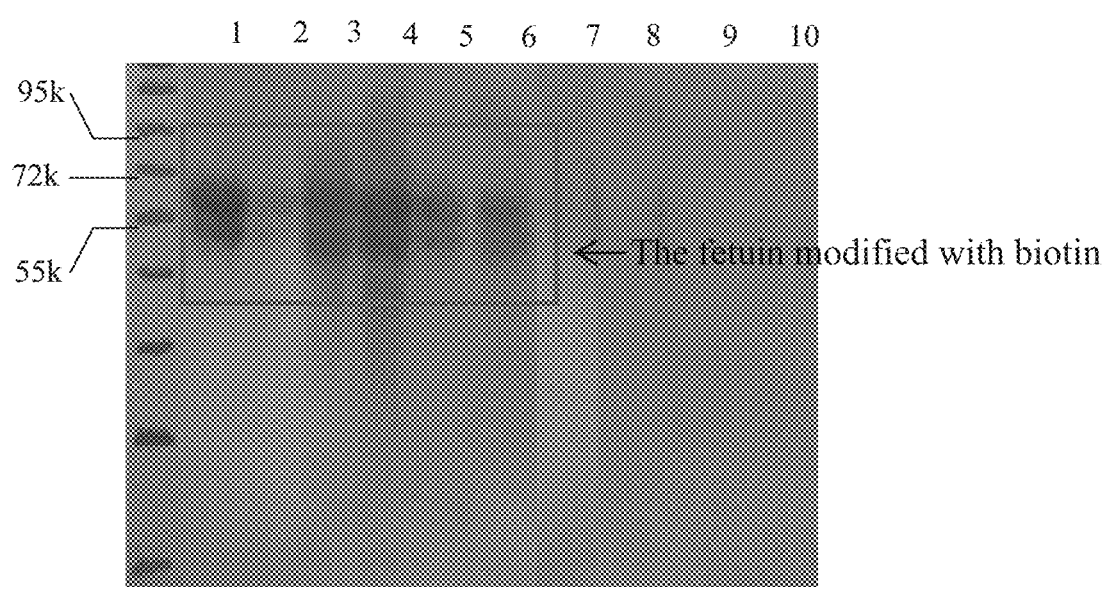
FIG. 4B is a SDS-PAGE stained by Western blot showing the efficiency of the modification of the glycosylated polypeptide in accordance with an embodiment of the present invention.
Figure 5A:
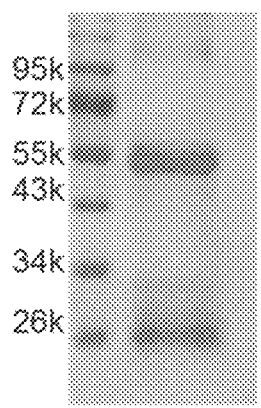
FIG. 5A is a SDS-PAGE stained by coomassie blue showing the efficiency of the modification of the antibody in accordance with an application example of the present invention.
Figure 5B:
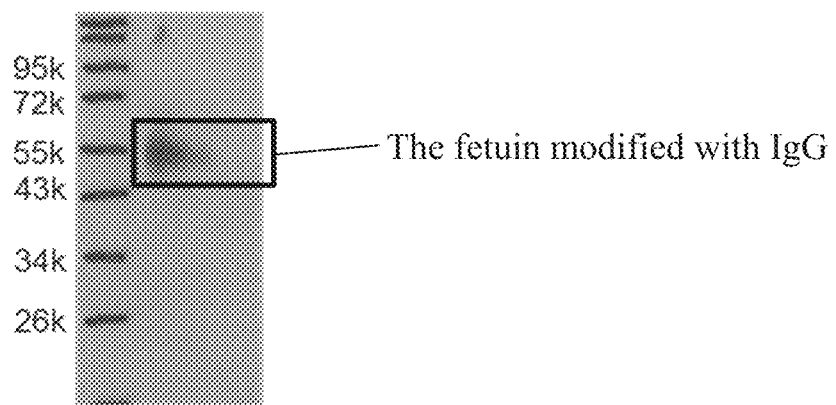
FIG. 5B is a SDS-PAGE stained by Western blot showing the efficiency of the modification of the antibody in accordance with an application example of the present invention.

Referring to FIGS. 4A to 4B and FIGS. 5A to 5B, in which the first to sixth lanes were the examples 1 to 6, the seventh to tenth lanes were the comparative examples 1 to 4, and FIGS. 5A to 5B were the example 7. The results of the coomassie brilliant blue gels in FIGS. 4A and 5A showed that the fetuin was in all the examples 1 to 6 and the comparative examples 1 to 4, and immunoglobulin G (IgG) was in the example 7. Besides, according to the results of Western blotting in FIGS. 4B and 5B, the fetuin or the immunoglobulin G could be modified by the modifying group (i.e., biotin) effectively only when the specific combination of the promoter claimed in the invention was used. The aforementioned specific combination was elaborate in the aforementioned paragraphs and would not be repeated herein. On the other hand, if the specific combination of the promoter claimed in the invention was not used as shown in the comparative examples 1 to 4, the glycosylated polypeptide could not be modified by the modifying group.

2. Modifying Specificity with Modifying Group

The modifying specificity with the modifying group referred herein the present invention was evaluated by using the antibody of the concanavalin A (Anti-Con A, bought from Vector Laboratories Inc., CA, USA) of the experiment 8 and the comparative example 5 as the glycosylated polypeptide and poly(n-isopropylacrylamide) (pNIPAAm) as the modifying group. Then, the anti-Con A modified with n-isopropylacrylamide reacted with the anti-Con A modified by the biotin. Next, unreacted anti-Con A was removed. After that, the concanavalin A was separated from the anti-con A, followed by Western blotting (using antibody such as the aforementioned biotin).

If the modification of the antibody constant region of the anti-con A with the poly(n-isopropylacrylamide) was specific, the reactivity between concanavalin A and anti-con A would be excellent, and the intensity of the band signal on the Western blotting gel would be relative high. Vice versa, if the modification with the poly(n-isopropylacrylamide) was not specific, the anti-con A would be modified by poly(n-isopropylacrylamide) at any sites, and the Fab region of the anti-con A that would react with the concanavalin A was blocked, which results in a bad reactivity between concanavalin A and anti-con A, and thus the intensity of the band signal on the Western blotting gel would be relative low.

It was noted that the band signals on the Western blotting band were located at 36 kDa, 72 kDa and 95 kDa, which were the monomer of the concanavalin A, the dimer of the concanavalin A and the trimer of the concanavalin A.

Figure 6A:
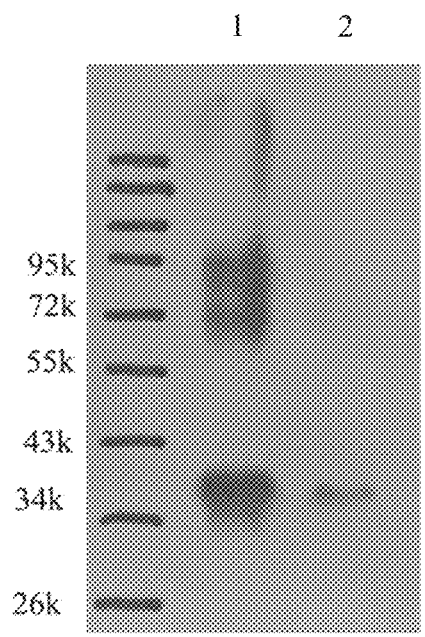
FIG. 6A is a SDS-PAGE stained by Western blot showing the efficiency of the modification of the antibody in accordance with another application example of the present invention.

Referring to FIG. 6A, which was the Western blotting results of the example 8 (the first lane) and the comparative example 5 (the second lane). In FIG. 6A, band signals with high intensities appeared at 36 kDa, 72 kDa and 95 kDa in the first lane, indicating that the modification of the anti-con A with the poly(n-isopropylacrylamide) had modifying specificity. However, only one band signal with a weak intensity appeared at 26 kDa in the second lane of the comparative example 5, indicating that the modification of the anti-con A of the comparative example 5 by poly(n-isopropylacrylamide) was not specific.

Figure 6B:
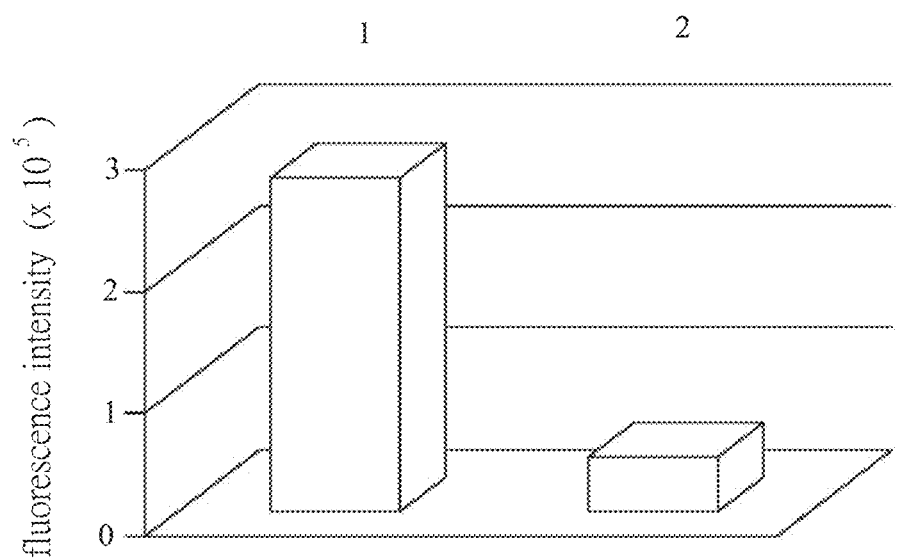
FIG. 6B is a bar chart showing the fluorescence intensity at 36 kDa in FIG. 6A.

Referring to FIG. 6B, which qualified the intensities of the band signals shown in the aforementioned FIG. 6A. As shown in FIG. 6B, the fluorescence intensity of the band signal with example 8 (the first lane) at 36 kDa was about $2.5 \times 10^5$. However, the fluorescence intensity of the band signal of the comparative example 5 (the second lane) with the same molecular weight was about $0.5 \times 10^5$, which was much weaker than that of the example 8. Thus, according to the results showed in FIGS. 6A to 6b, it was apparent that the method of the present invention was specific.

In practice with the method of sugar-guided modifying a glycosylated polypeptide and the application of the same, the sugar group on the glycosylated polypeptide is used for guiding, and the reaction of the probe molecule with the modifying group is controlled by the specific promoter. As a result, the binding of the glycosylated polypeptide to the probe molecule and the modification of the glycosylated polypeptide by the modifying group are performed in the individual steps. Therefore, the location adjacent to a sugar group can be modified by the modifying group. Thus, the method of the present invention can selectively modify a given site, thereby increasing the efficiency of the modification with modifying group as well as developing more application for the glycosylated polypeptide having the modifying group.

Although the present invention has been described in considerable detail with reference to certain embodiments thereof, other embodiments are possible. Therefore, the spirit and scope of the appended claims should not be limited to the description of the embodiments contained herein.

TABLE 1

| | | Examples | | | | | | | | Comparative examples | | | | |
|---|---|---|---|---|---|---|---|---|---|---|---|---|---|---|
| | | 1 | 2 | 3 | 4 | 5 | 6 | 7 | 8 | 1 | 2 | 3 | 4 | 5 |
| Glycosylated polypeptide (µM) | A-1 | 50 | 50 | 50 | 50 | 50 | 50 | — | — | 50 | 50 | 50 | 50 | — |
| | A-2 | — | — | — | — | — | — | 100 | — | — | — | — | — | — |
| | A-3 | — | — | — | — | — | — | — | 100 | — | — | — | — | 100 |
| Probe (µM) | B-1 | 500 | 500 | 500 | 500 | 500 | 500 | 100 | 100 | 500 | 500 | 500 | 500 | 100 |
| Modifying group (µM) | C-1 | 500 | 500 | 500 | 500 | 500 | 500 | — | — | 500 | 500 | 500 | 500 | — |
| | C-2 | — | — | — | — | — | — | — | 100 | — | — | — | — | 100 |
| Promoter Catalyst (mM) | D-1-1 | 1 | 1 | 1 | 1 | — | — | 0.1 | 0.1 | 1 | 1 | — | — | — |
| | D-1-2 | — | — | — | — | 1 | — | — | — | — | — | — | — | — |
| | D-1-3 | — | — | — | — | — | 1 | — | — | — | — | 1 | — | — |
| Catalyst stabilizer (mM) | D-2 | 1 | 1 | 1 | — | — | — | — | — | — | — | 1 | 1 | 1 |
| Reductant (mM) | D-3-1 | — | 1 | — | — | — | — | — | — | — | 1 | 1 | 1 | 1 |
| | D-3-2 | — | — | 1 | 1 | — | 1 | 0.1 | 0.1 | — | — | — | — | — |

A-1 Fetuin
A-2 Immunoglobulin G (IgG)
A-3 Con A
C-1 Biotin
C-2 poly(N-isopropylacrylamide) (pNIPAAm)
D-1-1 Tetrakis(acetonitrile)copper hexafluorophosphate [Cu(CH$_3$CN)$_4$PF$_6$]
D-1-2 Copper(I) iodide (CuI)
D-1-3 Copper(II) sulfate (CuSO$_4$)
D-2 Tris[(1-benzyl-1H-1,2,3-triazol-4-yl)methyl]amine (TBTA)
D-3-1 Tris(2-carboxyethyl)phosphine (TCEP)
D-3-2 Sodium ascorbate (NaAsc)

What is claimed is:

1. A method of sugar-guided modifying a glycosylated polypeptide, comprising:
providing a glycosylated polypeptide, wherein the glycosylated polypeptide comprises at least one amino acid having a nucleophilic residue;
reacting a boronic acid group of a probe molecule with a sugar group of the glycosylated polypeptide, so as to form a first intermediate product having a first covalent bond, wherein a molar concentration ratio of the glycosylated polypeptide and the probe molecule is 1:1000 to 1:1, and the probe molecule has a structure as shown in a formula (I):

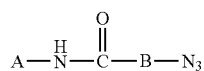
(I)

in the formula (I), the A has structures as shown in formulas (I-1-1) to (I-1-3), the B has a structure as shown in a formula (I-2), and sulfonyl group of the B binds to an azide group of the probe molecule,

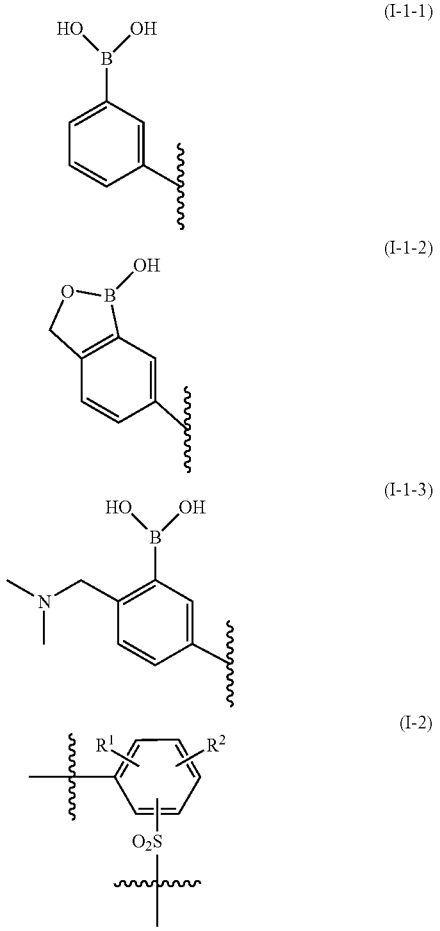

in the formula (I-2), the $R^1$ is a hydrogen atom, a halogen atom or an alkyl group with 1 to 3 carbon atoms, the $R^2$ is a hydrogen atom or a halogen atom;
reacting the azide group of the probe molecule with an alkyne group of a modifying group in the presence of a promoter, so as to form a second intermediate product having a second covalent bond, wherein the promoter comprises a catalyst, the catalyst is a metallic salt of monovalent copper or divalent copper, and the glycosylated polypeptide of the second intermediate product connects to the probe molecule via the first covalent bond and connects to the modifying group via the second covalent bond, respectively;
adding a polyol compound to form a third intermediate product, wherein the polyol compound is at least one selected from the group consisting of glycerol, sorbitol and polyethylene glycol (PEG), and the glycosylated polypeptide connects to the probe molecule and the modifying group via the second covalent bond in the third intermediate product; and
performing a hydrolysis reaction on the third intermediate product to release the probe molecule, thereby forming the glycosylated polypeptide having the modifying group.

2. The method of sugar-guided modifying a glycosylated polypeptide of claim 1, further comprising:
dissolving the glycosylated polypeptide and the probe molecule in a salt buffer;
removing an unreacted probe molecule after forming the first intermediate product having the first covalent bond; and
removing an unreacted modifying group after the hydrolysis reaction.

3. The method of sugar-guided modifying a glycosylated polypeptide of claim 1, wherein the catalyst is at least one selected from the group consisting of tetrakis(acetonitrile) copper(I) hexafluorophosphate [Cu(CH$_3$CN)$_4$PF$_6$], copper (I) iodide (CuI) and copper(II) sulfate (CuSO$_4$).

4. The method of sugar-guided modifying a glycosylated polypeptide of claim 1, wherein the promoter further comprises tris[(1-benzyl-1H-1,2,3-triazol-4-yl) methyl]amine (TBTA), 0.1 mM to 1 mM reductant or a combination thereof when the catalyst is tetrakis(acetonitrile)copper(I) hexafluorophosphate, and the reductant is tris(2-carboxyethyl)phosphine (TCEP) or sodium ascorbate (NaAsc).

5. The method of sugar-guided modifying a glycosylated polypeptide of claim 3, wherein the promoter further comprises a reductant when the catalyst is the copper(II) sulfate, and the reductant is tris(2-carboxyethyl)phosphine (TCEP) or sodium ascorbate (NaAsc).

6. The method of sugar-guided modifying a glycosylated polypeptide of claim 1, wherein the modifying group comprises a labeling reagent, a polymer with a number average molecular weight of 600 Da to 40 kDa, a polypeptide or an alkyl halide.

7. A reagent kit of sugar-guided antibody modification, comprising:
a target antibody, wherein an antibody constant region (Fc region) of the target antibody comprising a sugar group and at least one amino acid having a nucleophilic residue;
a probe molecule, wherein a molar concentration ratio of the target antibody and the probe molecule is 1:1000 to 1:1, and the probe molecule has a structure as shown in a formula (I):

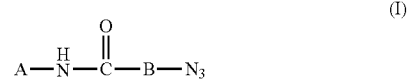
(I)

in the formula (I), the A has structures as shown in formulas (I-1-1) to (I-1-3), the B has a structure as shown in a formula (I-2), and sulfonyl group of the B binds to an azide group of the probe molecule,

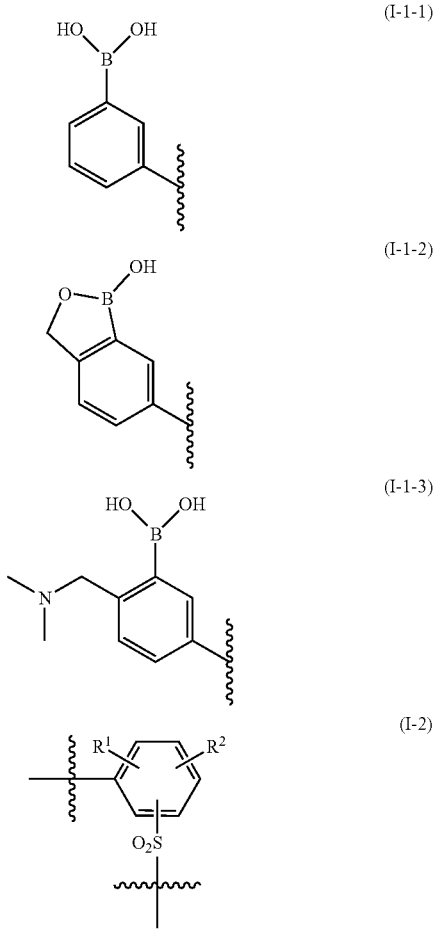

in the formula (I-2), the $R^1$ is a hydrogen atom, a halogen atom or an alkyl group with 1 to 3 carbon atoms, the $R^2$ is a hydrogen atom or a halogen atom, wherein a boronic acid group of the probe molecule and the sugar group of the target antibody form a first intermediate product having a first covalent bond;

a promoter comprising a catalyst, wherein the catalyst is selected from the group consisting of tetrakis(acetonitrile)copper(I) hexafluorophosphate [Cu(CH$_3$CN)$_4$PF$_6$], copper(I) iodide (CuI) and copper(II) sulfate (CuSO$_4$);

a modifying group having an alkyne group, wherein the alkyne group and the azide group of the probe molecule form a second intermediate product having a second covalent bond in presence of the catalyst, and in the second intermediate product, the target antibody connects to the probe molecule via the first covalent bond and connects to the modifying group via the second covalent bond, respectively;

a polyol compound for forming a third intermediate product, wherein the polyol compound is at least one selected from the group consisting of glycerol, sorbitol and polyethylene glycol, and the target antibody connects to the probe molecule and the modifying group via the second covalent bond; and a hydrolysis agent for performing a hydrolysis reaction on the third intermediate product to release the probe molecule, thereby forming the target antibody with an antibody constant region modified by the modifying group, wherein the hydrolysis agent is an acidic hydrolysis agent.

8. The reagent kit of sugar-guided antibody modification of claim 7, wherein the promoter further comprises tris[(1-benzyl-1H-1,2,3-triazol-4-yl) methyl]amine (TBTA), a reductant or a combination thereof when the catalyst is the tetrakis(acetonitrile)copper(I) hexafluorophosphate, and the reductant is tris(2-carboxyethyl)phosphine (TCEP) or sodium ascorbate (NaAsc).

9. The reagent kit of sugar-guided antibody modification of claim 7, wherein the promoter further comprises a reductant when the catalyst is the copper(II) sulfate, and the reductant is tris(2-carboxyethyl)phosphine (TCEP) or sodium ascorbate (NaAsc).

10. The reagent kit of sugar-guided antibody modification of claim 7, wherein the modifying group comprises a labeling reagent, a polymer with a number average molecular weight of 600 Da to 40 kDa, polypeptide or an alkyl halide.

11. The reagent kit of sugar-guided antibody modification of claim 7, further comprising a salt buffer.

12. A method of sugar-guided modifying an antibody, comprising:

providing a target antibody, wherein an antibody constant region (Fc region) of the target antibody comprising a sugar group and at least one amino acid having a nucleophilic residue;

reacting a boronic acid group of a probe molecule with a sugar group of the target antibody, so as to form a first intermediate product having a first covalent bond, wherein a molar concentration ratio of the target antibody and the probe molecule is 1:1000 to 1:1, and the probe molecule has a structure as shown in a formula (I):

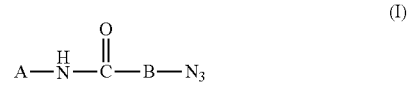

in the formula (I), the A has structures as shown in formulas (I-1-1) to (I-1-3), the B has a structure as shown in a formula (I-2), and sulfonyl group of the B binds to an azide group of the probe molecule,

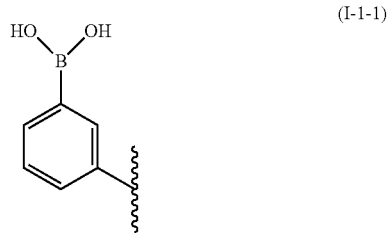

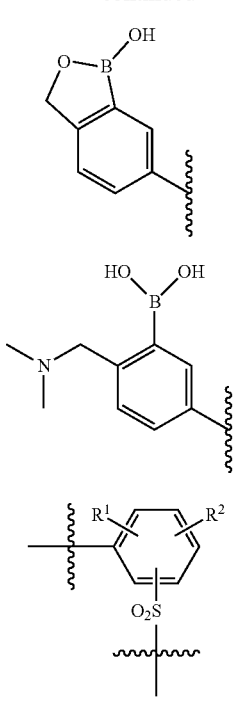

in the formula (I-2), the $R^1$ is a hydrogen atom, a halogen atom or an alkyl group with 1 to 3 carbon atoms, the $R^2$ is a hydrogen atom or a halogen atom;

reacting the azide group of the probe molecule with an alkyne group of a modifying group in presence of a promoter, so as to form a second intermediate product having a second covalent bond, wherein the promoter comprises a catalyst, the catalyst is a metallic salt of monovalent copper or divalent copper, and the target antibody of the second intermediate product connects to the probe molecule via the first covalent bond and connects to the modifying group via the second covalent bond, respectively;

adding a polyol compound to form a third intermediate product, wherein the polyol compound is at least one selected from the group consisting of glycerol, sorbitol and polyethylene glycol, and the target antibody connects to the probe molecule and the modifying group via the second covalent bond in the third intermediate product; and performing a hydrolysis reaction on the third intermediate product, so as to release the probe molecule, thereby forming the target antibody with an antibody constant region modified by the modifying group.

13. The method of sugar-guided modifying the antibody of claim 12, further comprising:
dissolving the target antibody and the probe molecule in a salt buffer;
removing an unreacted probe molecule after forming the first intermediate product having the first covalent bond; and
removing an unreacted modifying group after the hydrolysis reaction.

14. The method of sugar-guided modifying the antibody of claim 12, wherein the catalyst is at least one selected from the group consisting of tetrakis(acetonitrile)copper(I) hexafluorophosphate [Cu(CH$_3$CN)$_4$PF$_6$], copper(I) iodide (CuI) and copper(II) sulfate (CuSO$_4$).

15. The method of sugar-guided modifying the antibody of claim 12, wherein the promoter further comprises tris[(1-benzyl-1H-1,2,3-triazol-4-yl) methyl]amine (TBTA), a reductant or a combination thereof when the catalyst is tetrakis(acetonitrile)copper(I) hexafluorophosphate, and the reductant is tris(2-carboxyethyl)phosphine (TCEP) or sodium ascorbate (NaAsc).

16. The method of sugar-guided modifying the antibody of claim 15, wherein the promoter further comprises a reductant when the catalyst is the copper(II) sulfate, and the reductant is the tris(2-carboxyethyl)phosphine (TCEP) or the sodium ascorbate (NaAsc).

17. The method of sugar-guided modifying the antibody of claim 12, wherein the modifying group comprises a labeling reagent, a polymer with a number average molecular weight of 600 Da to 40 kDa, a polypeptide or an alkyl halide.

* * * * *